(12) United States Patent
LeConte

(10) Patent No.: US 7,915,403 B2
(45) Date of Patent: Mar. 29, 2011

(54) PRODUCTION OF LACTAMS

(75) Inventor: Philippe LeConte, Meyzieu (FR)

(73) Assignee: Rhodia Chimie, Aubervilliers (FR)

( * ) Notice: Subject to any disclaimer, the term of this patent is extended or adjusted under 35 U.S.C. 154(b) by 505 days.

(21) Appl. No.: 11/884,883

(22) PCT Filed: Feb. 14, 2006

(86) PCT No.: PCT/FR2006/000331
§ 371 (c)(1),
(2), (4) Date: Sep. 9, 2008

(87) PCT Pub. No.: WO2006/090044
PCT Pub. Date: Aug. 31, 2006

(65) Prior Publication Data
US 2009/0234115 A1    Sep. 17, 2009

(30) Foreign Application Priority Data
Feb. 22, 2005    (FR) ..................................... 05 01761

(51) Int. Cl.
*C07D 201/08*    (2006.01)

(52) U.S. Cl. ...................................................... 540/539
(58) Field of Classification Search .................... 540/539
See application file for complete search history.

(56) References Cited

U.S. PATENT DOCUMENTS

| | | | |
|---|---|---|---|
| 4,470,928 A | 9/1984 | Kimura et al. | |
| 6,100,396 A | 8/2000 | Gayet et al. | |
| 6,365,770 B1 | 4/2002 | Bunel et al. | |
| 2003/0153749 A1 | 8/2003 | Ohlbach et al. | |

FOREIGN PATENT DOCUMENTS

| | | |
|---|---|---|
| EP | 0 023 751 B1 | 2/1981 |
| WO | WO 98/05636 A1 | 2/1998 |
| WO | WO 98/37063 A1 | 8/1998 |

*Primary Examiner* — Bruck Kifle
(74) *Attorney, Agent, or Firm* — Bunchanan Ingersoll & Rooney PC

(57) ABSTRACT

Lactams, notably $\epsilon$-caprolactam, are prepared from alkyl cyanovalerates, themselves obtained from unsaturated nitrile compounds, by contacting same, in gaseous state, with hydrogen in the presence of hydrogenation/cyclization catalysts, and then condensing the gas stream thus formed, without intermediate separation of any alkyl aminocaproate, and recovering lactam produced therefrom.

17 Claims, No Drawings

PRODUCTION OF LACTAMS

CROSS-REFERENCE TO PRIORITY APPLICATIONS

This application is the United States national phase of International Application No. PCT/FR 2006/000331, filed Feb. 14, 2006, published in French as International Publication No. WO 2006/090044 A1 on Aug. 31, 2005, and claims priority of French Application No. 0501761, filed Feb. 22, 2005, each hereby expressly incorporated by reference in its entirety and each assigned to the assignee hereof.

The present invention relates to a process for the manufacture of lactams.

It relates more particularly to a process for the manufacture of lactams from alkyl cyanovalerate compounds obtained by using, as starting materials, in particular unsaturated mononitrile compounds and more particularly pentenenitriles, such as 2-, 3- or 4-pentenenitrile, taken in isolation or as a mixture, and referred to below as PN for the mixture and 2PN, 3PN and 4PN respectively.

ε-Caprolactam is a compound used preferentially for the manufacture of various polyamides, the most important of which is polyamide 6 (PA 6) or polycaproamide.

Several processes for the synthesis of ε-caprolactam have been provided, some of which have been made use of industrially for many years. The most widely used process employs benzene as starting material for the manufacture of cyclohexanone oxime as intermediate compound, the ε-caprolactam being obtained by the Beckmann rearrangement reaction.

A process for the manufacture of ε-caprolactam using butadiene as starting material and with a adiponitrile as intermediate compound has also been provided for several years.

In this process, the adiponitrile, obtained by double hydrocyanation of the butadiene, is partially hydrogenated to give aminocapronitrile with joint production of hexamethylenediamine.

The aminocapronitrile, after separation, is hydrolysed and cyclized to give caprolactam, either in the gas phase or in the liquid phase, in the presence or absence of a solvent. This process requires double hydrocyanation of the butadiene and produces hexamethylenediamine in conjunction, which has to be recovered in value for the economics of the process.

It is also possible, starting from butadiene, to carry out an alkoxycarbonylation, in order to obtain the alkyl pentenoate, and then a hydroformylation, followed by reductive amination to give alkyl aminocaproate. The latter compound is subsequently cyclized to give caprolactam.

A process for the synthesis of caprolactam using butadiene as starting material and pentenenitriles (PNs), obtained by a simple hydrocyanation of one double bond of the butadiene, as intermediate compound has also been provided. In this process, the PNs are converted to formylvaleronitrile in a hydroformylation reaction in the presence of hydrogen and carbon monoxide.

This formylvaleronitrile is subsequently converted, in a second stage, to alkyl cyanovalerate by oxidation and reaction with an alcohol.

After isolation, for example by distillation, the alkyl cyanovalerate is hydrogenated to produce the alkyl aminocaproate. Caprolactam is obtained in a final stage by cyclization of the alkyl aminocaproate.

Such a process, disclosed in particular in U.S. Pat. No. 6,365,770, comprises numerous successive stages requiring, between each stage, separation of the intermediate compound formed.

These various separation stages result in a loss in overall yield of the process and thus greatly affect the economics of the process.

This sequence of successive reactions and stages is described in numerous patents and papers, such as, for example, Patent WO 01/96294.

One of the aims of the present invention is to overcome these disadvantages by providing a process which makes it possible to improve its overall yield and to reduce the capital costs necessary for the industrial operation of the process.

To this end, the invention provides a process for the synthesis of caprolactam starting from alkyl cyanovalerate which is characterized in that it consists in bringing the alkyl cyanovalerate, in the gas state, into contact with hydrogen in the presence of hydrogenation and cyclization catalysts, in recovering the gas stream comprising the caprolactam formed and in treating the said stream, after condensation, in order to recover the caprolactam.

The process of the invention makes it possible to obtain the caprolactam directly from the alkyl cyanovalerate without a stage of isolation and of recovery of the alkyl aminocaproate formed in situ.

For this reason, the capital costs necessary for the operation of this process are significantly reduced, as are the losses in products which arise during the stages of separation of the alkyl aminocaproate or by polymerization reactions.

According to a preferred embodiment of the invention, the process applies more particularly to the synthesis of ε-caprolactam from an alkyl cyanovalerate, such as methyl cyanovalerate.

According to another characteristic of the invention, the treatment of the gas stream at the outlet of the reactor consists in condensing the gas stream and in treating it in order to separate the various components and to recover the caprolactam. By way of example, the condensed stream can be treated with ion-exchange resins. The medium obtained comprising the caprolactam, after treatment on resin, is distilled in the presence of a strong base in order to separate the alcohol and/or the solvent and to recover the caprolactam.

Such a process for the treatment of a cyclization medium in order to obtain pure caprolactam is disclosed in particular in Patent EP 922 027.

It is also possible, without departing from the scope of the invention, to use any known process which makes it possible to extract and purify the caprolactam present in a medium.

Thus, this extraction and/or purification can comprise crystallization, hydrogenation or oxidation stages, for example.

The alkyl cyanovalerate used as starting material in the process of the invention can be obtained, for example, from pentenenitriles by a hydroformylation reaction and then oxidation and reaction with an alcohol, as disclosed, by way of indication, in U.S. Pat. Nos. 6,365,770, 5,986,126 and WO 00/56451.

The alkyl cyanovalerate can also be obtained by alkoxycarbonylation of the pentenenitriles by reaction with carbon monoxide and an alcohol, such as methanol. Such processes are disclosed in Patents WO 01/72697, WO 03/040159 and WO 00/14055.

Other manufacturing processes are described, for example, in the paper by Reppe published in Lieb. Ann. Chem., 596 (1995), 127, and in Patents BE 850113 and EP 576976.

Generally, any known process for the synthesis of an alkyl cyanovalerate is suitable for the invention, such as the process using the enzymatic hydrolysis of adiponitrile disclosed in particular in Patent WO 97/44318.

According to the invention, the conversion of the alkyl cyanovalerate to caprolactam is carried out in a single reactor comprising a catalytic system exhibiting, on the one hand, a catalytic activity for the hydrogenation and, on the other hand, a catalytic activity for the cyclization reaction.

According to one embodiment of the invention, the hydrogenation and cyclization catalysts are separate components which are present in the reactor in the form of a mixture of solid granules or powders or in the form of catalytic beds, in particular when the reactor is tubular or in the column form. In the latter embodiment, the two catalytic beds are advantageously positioned in a successive and adjacent fashion in the reactor, the bed of hydrogenation catalyst being positioned upstream of the bed of cyclization catalyst in the direction of the movement of the gases or vapours constituting the reaction stream. The reactor can also comprise a single catalytic bed comprising a mixture of the two catalysts.

In another embodiment of the invention, the single catalytic system is composed of a supported catalyst, the support advantageously being a cyclization catalyst and the metals catalysing the hydrogenation being deposited or absorbed on the said support.

Mention may be made, as examples of hydrogenation catalysts which can be used in the form of a mixture or in the form of a catalytic bed, of the catalysts comprising, as active metal element, iron, ruthenium, rhodium, iridium, palladium, cobalt, nickel, chromium, osmium and platinum, or a mixture of these. These metals can be used in the form of supported catalysts or in bulk form. Such catalysts are disclosed in particular in Patents US 2003/0153749 and U.S. Pat. No. 6,365,770.

Generally, all catalytic supports are suitable for producing these hydrogenation catalysts. One or more metals are deposited at the surface of these supports, in particular in the oxide form. The amount of metal on the support is not critical but is generally between 0.1% and 50% by weight, with respect to the weight of supported catalyst.

As regards the cyclization reaction, the suitable catalysts are solid heterogeneous catalysts, such as those disclosed, for example, in European Patent Application 1 456 177.

Among the catalysts disclosed in this document, metal oxides, such as aluminas or silica, zeolites or metal phosphates, such as, for example, aluminium phosphates, titanium phosphates or zirconium phosphates, are particularly suitable for the invention.

Mention will be made, as preferred cyclization catalysts of the invention, of porous aluminas, in particular those disclosed in European Patents Nos. 0 805 801 and 1 098 875.

According to one embodiment of the invention, the catalytic system is advantageously a single catalyst which comprises a catalytic activity for the hydrogenation reaction and a catalytic activity for the cyclization reaction. The preferred catalysts of the invention exhibiting these activities are catalysts obtained by deposition of one or more metal elements, which exhibit a catalytic activity in hydrogenation and which are described above, on a solid compound corresponding to the cyclization catalysts described above. Thus, the preferred catalysts of the invention are the catalysts comprising a metal oxide, such as the porous aluminas described above, on which is deposited at least one catalytically active metal element. These catalysts can be obtained by any conventional process for the manufacture of supported catalysts.

According to the invention, it is possible to carry out the hydrogenation and cyclization reactions in the presence of ammonia and/or of water. Advantageously, the concentration by weight of ammonia and/or of water in the reaction medium is between 5 and 40%. These reactions are carried out at a temperature of between 200° C. and 450° C. and advantageously under a hydrogen partial pressure of between 0.1 and 20 bar.

The lactam according to the process of the invention can be manufactured in any reactor which makes possible the reaction between gases by passing over a catalyst advantageously in the solid state.

Thus, the preferred reactors are tubular reactors or column reactors which can comprise stationary or fluidized beds of catalysts.

The gas stream at the outlet of the reactor is advantageously rapidly cooled in order to prevent the formation of oligomers by polymerization of the lactam.

The lactam recovered is subsequently purified and recovered according to known purification processes. Thus, in one embodiment of the invention, the gas stream exiting from the reactor is rapidly condensed and cooled to a temperature of less than 150° C. This condensation and cooling stage is carried out over a time of between a few seconds and a few minutes. The ammonia which may be present is subsequently removed by distillation. The resulting medium, comprising the caprolactam in solution in the alcohol formed (methanol in the case of methyl cyanovalerate) or in an aqueous/methanolic medium, is subsequently purified by treatment on resins, hydrogenation, oxidation, crystallization and/or distillation. The caprolactam recovered exhibits a comparable degree of purity to that obtained by the various known synthetic processes.

Other advantages and details of the invention will become more clearly apparent in the light of the examples given below purely by way of illustration.

EXAMPLES 1 TO 5

The tests were carried out in a cylindrical reactor composed of a glass tube equipped with electrical heating means, with a temperature measurement probe, with an inlet and an outlet for the gases and with a means for introducing the reactant.

The glass tube, in the vertical position, is filled successively, from the bottom upwards, with 5 ml of quartz beads, 4 ml of catalyst A, 4 ml of catalyst B and 5 ml of quartz beads. Depending on the examples, catalyst A is composed of a hydrolysis catalyst and catalyst B is a hydrogenation catalyst, or catalysts A and B are identical and constitute a mixed catalyst composed of a metal element deposited on a support generally and preferably of alumina.

The reactor is heated at 300° C. under a stream of hydrogen fed via the top of the reactor with a flow rate of 2.5 l/h. After one hour, the methanolic solution of methyl cyanovalerate (the reactant) is fed in the hydrogen stream with a flow rate of 2 ml/h. This solution comprises 60% by weight of methyl cyanovalerate.

The vapours collected at the outlet of the reactor are condensed and analysed by gas chromatography using butylbenzene as internal standard.

The degree of conversion (DC) of the methyl cyanovalerate and the yield (RY) of caprolactam are calculated from the results of the analyses.

The results obtained are collated in the table below:

| Ex. | Catalyst | | DC (%) | RY (%) | |
| --- | --- | --- | --- | --- | --- |
| | A | B | | | |
| 1 | $Al_2O_3$ * | $Ni/Al_2O_3$ | 98 | 37 | (1) |
| 2 | $Al_2O_3$ * | $Rh/Al_2O_3$ | 100 | 45 | (2) |

-continued

| | Catalyst | | | | |
|---|---|---|---|---|---|
| Ex. | A | B | DC (%) | RY (%) | |
| 3 | Pt/Al$_2$O$_3$ | Pt/Al$_2$O$_3$ | 93 | 33 | (2) |
| 4 | Al$_2$O$_3$ * | Pd/Al$_2$O$_3$ | 100 | 37 | (2) |
| 5 | Al$_2$O$_3$ * | Rh/Al$_2$O$_3$ | 86 | 57 | (2), (3) |

* Al$_2$O$_3$ is an alumina with a pore volume of 117 ml/100 g and a specific surface of 139 m$^2$/g sold by Axens
(1) Catalyst sold by Johnson Mattey
(2) Catalysts sold by Engelhard comprising 0.5% by weight of metal element
(3) The methyl cyanovalerate is fed in the pure form (without solvent)

The invention claimed is:

1. A process for the preparation of caprolactam, comprising contacting an alkyl cyanovalerate, in gaseous state, with hydrogen in the presence of hydrogenation and cyclization catalysts, and then condensing the gas stream thus formed and recovering caprolactam produced therefrom.

2. The process as defined by claim 1, said hydrogenation catalyst comprising an active metal element selected from the group consisting of iron, ruthenium, rhodium, iridium, palladium, cobalt, nickel, chromium, osmium, platinum, or mixture thereof.

3. The process as defined by claim 2, said cyclization catalyst comprising a metal oxide, zeolite or metal phosphate.

4. The process as defined by claim 3, said cyclization catalyst comprising an alumina, silica, aluminum phosphate, zirconium phosphate or titanium phosphate.

5. The process as defined by claim 1, carried out in the presence of a hydrogenation/cyclization mixed catalyst.

6. The process as defined by claim 1, carried out in reactor wherein the hydrogenation catalyst and the cyclization catalyst are separately positioned and form two successive catalytic beds.

7. The process as defined by claim 5, said hydrogenation/cyclization mixed catalyst comprising a compound forming the cyclization catalyst and a catalytically active metal forming the hydrogenation catalyst deposited onto or impregnated in said cyclization catalyst compound.

8. The process as defined by claim 7, said hydrogenation/cyclization mixed catalyst comprising an alumina support forming the cyclization catalyst and having at least one metal element selected from the group consisting of iron, ruthenium, rhodium, iridium, palladium, cobalt, nickel, chromium, osmium, platinum, or mixture thereof, deposited thereon or impregnated therein.

9. The process as defined by claim 1, said alkyl cyanovalerate comprising methyl cyanovalerate.

10. The process as defined by claim 1, carried out at a temperature ranging from 200° C. to 450° C.

11. The process as defined by claim 1, carried out under a hydrogen pressure ranging from 0.1 to 20 bar.

12. The process as defined by claim 1, comprising treating the condensed gas stream thus formed with an ion-exchange resin or distilling same in the presence of a strong acid.

13. The process as defined by claim 1, comprising condensing the gas stream thus formed and distilling the caprolactam therefrom in the presence of a strong acid.

14. The process as defined by claim 12, comprising extracting ammonia, if present, from the condensed gas stream prior to the treatment thereof with said ion-exchange resin or distillation in the presence of a strong acid.

15. The process as defined by claim 1, carried out in the presence of ammonia and/or of water.

16. The process as defined by claim 1, said alkyl cyanovalerate having been obtained from an unsaturated mononitrile compound.

17. The process as defined by claim 1, carried out without intermediate separation of any alkyl aminocaproate formed in the process.

* * * * *